(12) United States Patent
Liu et al.

(10) Patent No.: US 7,371,885 B2
(45) Date of Patent: May 13, 2008

(54) CIS-TRANS ISOMERISATION OF SEMICARBAZONE COMPOUNDS

(75) Inventors: Weiguo Liu, Parsippany, NJ (US); Philip Harrington, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 183 days.

(21) Appl. No.: 10/578,465

(22) PCT Filed: Nov. 12, 2004

(86) PCT No.: PCT/EP2004/012872

§ 371 (c)(1), (2), (4) Date: May 8, 2006

(87) PCT Pub. No.: WO2005/047235

PCT Pub. Date: May 26, 2005

(65) Prior Publication Data

US 2007/0135520 A1    Jun. 14, 2007

Related U.S. Application Data

(60) Provisional application No. 60/519,621, filed on Nov. 14, 2003.

(51) Int. Cl.
*C07C 281/14* (2006.01)
*C07B 57/00* (2006.01)
(52) U.S. Cl. .......................... 558/417; 564/36
(58) Field of Classification Search ............ 558/417; 564/36
See application file for complete search history.

(56) References Cited

U.S. PATENT DOCUMENTS 3,136,794 A    6/1964  Maxwell, III et al.
5,543,573 A *  8/1996  Takagi et al. ............... 514/590
6,903,237 B2 * 6/2005  Yamaguchi et al. .......... 564/20
2007/0203356 A1* 8/2007  Zierke et al. ............... 558/410

FOREIGN PATENT DOCUMENTS

EP    0 462 456 A1    12/1991
GB    1117037          6/1968

OTHER PUBLICATIONS

Karabatsos et al., "Syn-anti isomer determination of 2,4-dinitrophenylhydrazones and semicarbazones by N. m. r.," Journal of the American Chemical Society, vol. 48:pp. 753-755 (Mar. 5, 1962) (XP002320013), Cited in Search Report.

Karabatsos, et al., "Structural studies by nuclear resonance. VIII. Ring-Substituted Phenylhydrazones, Semicarbazones, and Thiosemicarbazones," Journal of the American Chemical Society, vol. 86:pp. 3351-3357 (Aug. 20, 1964) (XP002320014), Cited in Search Report.

"Houben-weyl, Methoden der Organischen Chemi" vol. X/2:pp. 479-487 (1967) (XP002320015), Cited in Search Report.

* cited by examiner

*Primary Examiner*—Fiona T Powers
(74) *Attorney, Agent, or Firm*—Hutchison Law Group PLLC

(57) ABSTRACT

The present invention relates to the isomerization of the Z-isomer I-Z of semicarbazone compounds of the general formula (I) into its E-isomer I-E, where the variables in formula (I) have meanings given in claim 1

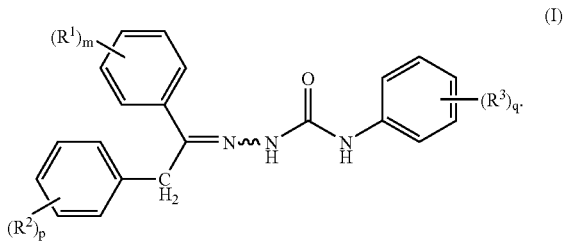

8 Claims, No Drawings

CIS-TRANS ISOMERISATION OF SEMICARBAZONE COMPOUNDS

This application is a National Stage application of International Application No. PCT/EP2004/012872 filed Nov. 12, 2004, which claims the benefit of U.S. Provisional Application No. 60/519,621, filed Nov. 14, 2003, the entire contents of which is hereby incorporated herein by reference in its entirety.

BACKGROUND OF THE INVENTION

The present invention relates to the isomerisation of the Z-isomer I-Z of semicarbazone compounds of the general formula I into its E-isomer I-E

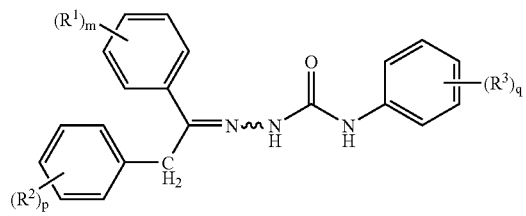
(I)

where the variables in formula I have the following meanings:

m, p and q are each independently an integer of 0, 1, 2, 3 or 4

$R^1$, $R^2$, $R^3$ are each independently halogen; OH; CN; $NO_2$;
  $C_1$-$C_6$-alkyl, optionally substituted with $C_1$-$C_4$-alkoxy, $C_1$-$C_4$-haloalkoxy or $C_3$-$C_6$-cycloalkyl;
  $C_1$-$C_6$-haloalkyl;
  $C_3$-$C_6$-cycloalkyl;
  $C_1$-$C_6$-alkoxy, optionally substituted with $C_1$-$C_4$-alkoxy or $C_3$-$C_6$-cycloalkyl;
  $C_1$-$C_6$-haloalkoxy;
  $C_1$-$C_6$-alkylcarbonyl;
  $C_3$-$C_6$-cycloalkoxy;
  $C_1$-$C_6$-alkoxycarbonyl or
  $C_1$-$C_6$-alkoxycarbonyloxy.

Semicarbazone compounds of the general formula I are known from EP-A-462456 to be effective as pest-controlling agents. Semicarbazones of the formula I have two geometrical isomers with regard to the C=N-double bond, namely the E-form I-E and the Z-form I-Z.

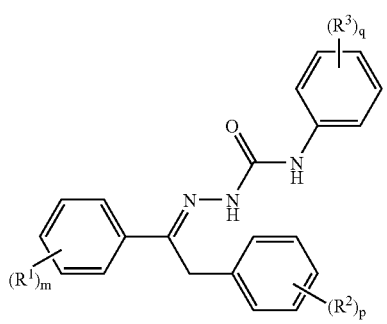
(I-E)

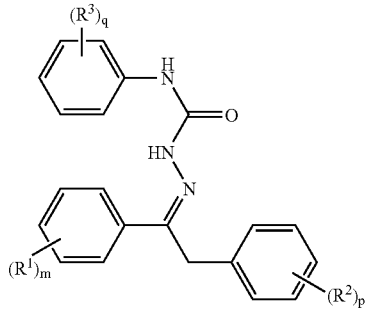
(I-Z)

At room temperature these geometrical isomers are stable with regard to E/Z-isomerisation. As regards the relative pesticidal activity of these compounds, the E-form I-E is generally more active than the Z-form I-Z. Therefore, agriculturally and commercially acceptable specifications of semicarbazones I require an E/Z-ratio of at least 9:1 and preferably at least 10:1.

Compounds of the formula I can be prepared by the process illustrated in the following scheme:

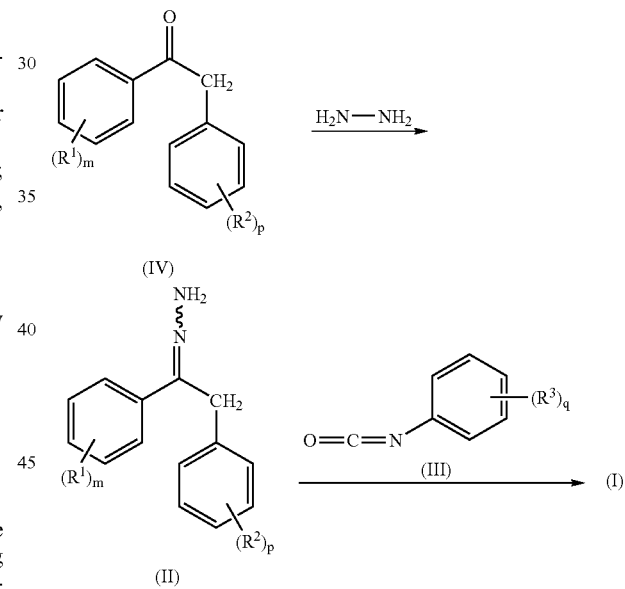

Significant amounts of the undesired Z-isomer I-Z are formed by this process. Moreover, much effort is needed to achieve the desired E/Z-ratio. Firstly, long reaction times are required to achieve a high E/Z-ratio in the hydrazone precursor II, necessary for obtaining the desired E/Z-ratio in the final product I. Secondly, the crystallisation of the E-isomer I-E in the presence of the Z-isomer I-Z is tedious and difficult. In order to obtain a high isolated yield of the desired E-isomer, some of the Z-isomer must also be crystallized with the E-isomer from the reaction mixture. Similarly, in order to obtain the desired E/Z-ratio in the crystallized product, a low isolated yield of the E-isomer is necessary, so that the undesired Z-isomer is completely solubilised along with significant amount of E-isomer in the reaction mixture. Thirdly, recrystallisation of isolated product I containing significant amounts of the undesired Z-isomer to obtain the desired E/Z-ratio is also tedious and difficult. As with crystallisation from the reaction mixture, either low crystallisation recoveries or high Z-isomer content of the final product are obtained.

These involve the risk of either isolating a product in low yield or not having not required E/Z-ratio.

Consequently, there is a need for a method which allows a simple isomerisation of the Z-isomer of I into its E-isomer I-E.

SUMMARY OF INVENTION

The inventors of the present invention have surprisingly found that the Z-isomer of the compound I can be isomerised into the E-isomer of I by reacting the Z-form I-Z or a mixture of the geometric isomers I-E and I-Z in the presence of iodine. This result was quite astonishing since irradiation of mixtures of the geometrical isomers I-Z and I-E predominately leads to the Z-isomer I-Z.

Therefore, the present invention relates to a process for the isomerisation of the Z-isomer I-Z of a compound of the general formula I as defined above into its E-isomer I-E by reacting Z-isomer I-Z or a mixture of the geometrical isomers I-Z and I-E in the presence of iodine.

DETAILED DESCRIPTION OF INVENTION

In general, about 0.1% by weight, preferably at least 0.2% by weight and more preferably at least 0.5% by weight of iodine, based on the total amount of the compound I, are required to achieve an isomerisation within acceptable reaction times. For practical reasons, the amount of iodine will not exceed 10% by weight and preferably not 5% by weight, based on the total amount of the compound I. Most preferably the isomerisation is carried out in the presence of 1 to 4% by weight of iodine.

In general, the reaction temperature will be at least 40° C., preferably at least 50° C. and more preferably at least 60° C. to achieve an isomerisation within an acceptable reaction time. For practical reasons, the reaction temperature in general will not exceed 150° C. and preferably not 100° C.

The process of the invention can be performed by starting from the almost pure Z-isomer I-Z (E/Z-ratio<5:95) or from mixtures of the geometrical isomers I-E and I-Z (E/Z-ratio>5:95). In a preferred embodiment of the present invention a mixture of the geometrical isomers I-E and I-Z having an E/Z-ratio ranging from 1:1 to 15:1, preferably from 2:1 to 15:1 and especially from 3:1 to 10:1 is used as a starting material.

In general, the isomerisation of I is performed until an E/Z-ratio of at least 95:5, preferably at least 97:3 and more preferably at least 98:2 is reached. The reaction time which is required to achieve the desired E/Z-ratio is in the range from 20 min. to 14 h, preferably 1 to 8 h and more preferably 2 to 4 h.

The isomerisation may be performed in an inert organic solvent or diluent. Suitable solvents are aromatic solvents such as benzene, toluene, xylenes, chlorobenzene, dichlorobenzene, acyclic ethers such as diethyl ether, methyl-tert.-butyl ether, alicyclic ethers such as tetrahydrofurane and dioxane, alkanols such as methanol, ethanol, propanol, isopropanol, n-butanol, ketones such as acetone and methylethyl ketone, nitriles such as acetonitrile and propionitrile, carbonates such as dimethylcarbonate, diethylcarbonate, ethylene carbonate and propylene carbonate, aliphatic and alicyclic hydrocarbons such as hexane, isohexane, heptane and cyclohexane and mixtures of the aforementioned solvents. Preferred solvents are the aforementioned aromatic solvents, especially toluene, xylene and mixtures of the aforementioned solvents which contain at least 50% by volume of the aforementioned aromatic solvents. In order to perform the isomerisation in an inert solvent or diluent, the Z-isomer I-Z or a mixture of the geometrical isomers I-E and I-Z can be dissolved or suspended in a suitable solvent and reacted in the presence of iodine as outlined above. It is also possible, to perform the isomerisation either in the reaction mixture obtained from the reaction of the hydrazone II and the isocyanate III or in the mother liquor obtained after crystallisation of the compound I from the reaction mixture.

In order to obtain the E-isomer I-E, optionally together with small amounts of Z-isomer I-Z, the isomerisation mixture is worked-up in a usual manner. Preferably, the isomer I-E, optionally together with small amounts of isomer I-Z (in general not more than 5% by weight) is isolated from the liquid reaction mixture by crystallisation or precipitation. Crystallisation or precipitation may be achieved either by cooling and/or concentration of the liquid reaction mixture and/or by the addition of an inert solvent which decreases the solubility of the compound I in the reaction mixture. Suitable solvents for decreasing the solubility of the compound I are aliphatic or alicyclic hydrocarbons such as hexane, heptane, isohexane and cyclohexane.

In another preferred embodiment of the present invention, the isomerisation of I-Z is performed in the absence of a solvent or diluent. In other words, the isomerisation of the Z-isomer I-Z is performed in the solid phase or in the melt-phase. Thus, the solid or molten compound I-Z or a solid or molten mixture of the geometrical isomers I-E and I-Z is reacted with iodine as outlined above. After the desired degree of isomerisation is achieved, the iodine can be simply removed by sublimation, e. g. by increasing the temperature and/or by applying reduced pressure. The residue usually contains only compound I having an increased E/Z-ratio with regard to the starting material and optionally those impurities contained in the starting material. The residue usually does not contain any further impurities.

Starting materials for the isomerisation in the absence of a solvent or diluent may be the pure Z-isomer or mixtures of the geometrical isomers I-E and I-Z. Examples of such mixtures are crystalline products which do not fulfil the required E/Z-ratio and the residue obtained from the mother liquor of the crystallisation of I during the work-up in the preparation of I.

The organic moieties mentioned in the above definitions of the variables are—like the term halogen—collective terms for individual listings of the individual group members. The prefix $C_n$-$C_m$ indicates in each case the possible number of carbon atoms in the group. The term halogen denotes in each case fluorine, bromine, chlorine or iodine, in particular fluorine or chlorine. Examples of other meanings are:

The term "$C_1$-$C_6$-alkyl" as used herein and the alkyl moieties of $C_1$-$C_6$-alkoxy, $C_1$-$C_6$-alkoxycarbonyl, $C_1$-$C_6$-alkylcarbonyl, and $C_1$-$C_6$-alkoxycarbonyloxy refer to a saturated straight-chain or branched hydrocarbon group having from 1 to 6 carbon atoms, especially from 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1, 2-trimethylpropyl, 1,2,2-trimethylpropyl, 1-ethyl-1-methylpropyl and 1-ethyl-2-methylpropyl. $C_1$-$C_4$-alkyl means for example methyl, ethyl, propyl, 1-methylethyl, butyl, 1-methylpropyl, 2-methylpropyl or 1,1-dimethylethyl.

In $C_1$-$C_6$-alkyl one hydrogen may be substituted by a radical, selected from $C_1$-$C_4$-alkoxy, $C_1$-$C_4$-haloalkoxy and $C_3$-$C_6$-cycloalkyl.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "$C_1$-$C_2$-fluoroalkyl" as used herein refers to a $C_1$-$C_2$-alkyl which carries 1, 2, 3, 4 or 5 fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term, "$C_1$-$C_6$-alkoxy" as used herein and the alkoxy moieties of $C_1$-$C_6$-alkoxycarbonyl, and $C_1$-$C_6$-alkoxycarbonyloxy refers to a straight-chain or branched saturated alkyl group having 1 to 6 carbon atoms (as mentioned above) which is attached via an oxygen atom to the remainder of the molecule. Examples include methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

In $C_1$-$C_6$-alkoxy one hydrogen may be substituted by a radical, selected from $C_1$-$C_6$-alkoxy and $C_3$-$C_6$-cycloalkyl.

The term "$C_1$-$C_6$-haloalkoxy" as used herein refers to a $C_1$-$C_6$-alkoxy group as mentioned above which is partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

The term "$C_3$-$C_6$-Cycloalkyl" as used herein refers to a cycloaliphatic radical having from 3 to 6 carbon atoms, such as cyclopropyl, cyclobutyl, cyclopentyl and cyclohexyl. The cycloalkyl radical may be unsubstituted or may carry 1 to 6 $C_1$-$C_4$ alkyl radicals, preferably a methyl radical.

In general, the isomerisation can be performed on any of the compounds of the formula I. In a preferred embodiment of the invention the variables m, p and q are each 1.

Preferred radicals $R^1$, $R^2$, $R^3$ are each independently halogen, CN, $C_1$-$C_6$-alkyl, $C_1$-$C_6$-haloalkyl, $C_1$-$C_6$-alkoxy or $C_1$-$C_6$-haloalkoxy. More preferably $R^1$ is halogen or $C_1$-$C_4$-haloalkyl, especially $CF_3$, $R^2$ is CN and $R^3$ is $C_1$-$C_4$-haloalkoxy, especially $OCF_3$.

An example of an especially preferred compound I is a compound where $R^1$ is $CF_3$ located in the 3-position of the phenyl ring, $R^2$ is CN located in the 4-position of the phenyl ring and $R^3$ is $OCF_3$ located in the 4-position of the phenyl ring. This compound is referred to as I.1, the isomers are referred to as I.1-E and I.1-Z:

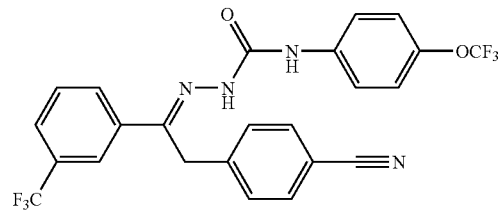

(I.1-E)

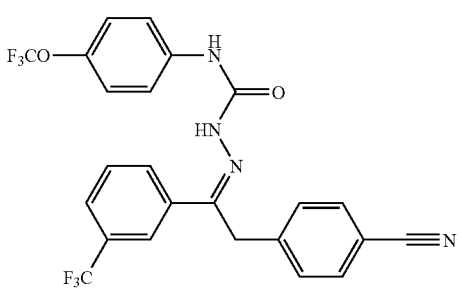

(I.1-Z)

The process of the present invention allows an easy isomerisation of the Z-isomer I-Z into its E-isomer I-E. The isomerisation usually yields a high E/Z-ratio which exceeds 95:5, preferably 97:3 and more preferred 98:2. No noticable amounts of by-products are formed, i. e. the yield of compound I is >99%. Therefore, the process of the present invention can be used to simplify the preparation of compounds I with the desired E/Z-ratio of $\geq 9:1$.

The following examples are intended to illustrate the present invention without limiting its scope.

EXAMPLE 1

Conversion of the pure Z-Form of compound I.1 into its E-form.

A mixture of 2 g of the Z-isomer I.1-Z and 0.04 g of iodine were heated at 90° C. in a sealed tube. Liquid chromatography (see below) show the product contains 97.8% of the E-isomer I.1-E and 2.2% of the Z-isomer I.1-Z (E/Z-ratio 97.8:2.2). The iodine was then removed in vacua at 90° C.

for two hours. The recovery yield was 100%. No other impurities could be detected by liquid chromatography.

Liquid chromatography: column: reversed phase RP 8-column, Kromasil 100-3.5C8; element: acetonitril/(water+0.1% trifluorolectic acid, pH 2.4) gradient; detection: UV 2235.4 nm.

EXAMPLE 2

Treatment of a crude reaction mixture containing 97.3% of compound I.1 having an E/Z-ratio of about 4.9:1.

2 g of a solid containing about 97.3% of compound I.1 having an E/Z-ratio of about 4.9:1 and 0.04 g of iodine were heated at 90° C. in a sealed tube for two hours. The iodine was then removed in vacuo by drying at 90° C. overnight. The recovery yield is about 100%. No additional impurities could be detected. The product contained 95.9% by weight of the E-isomer I.1-E and 1.4% by weight of the Z-isomer I.1-Z as determined by liquid chromatography (E/Z-ratio 68.5:1).

EXAMPLE 3

Conversion of Pure Z-Form of Compound I.1.

2 g of compound I.1-Z and 0.1 g of iodine were suspended in 8 g of chlorobenzene and the resulting slurry was heated at 60° C. for six hours. Then the reaction mixture was cooled and 10 g of hexanes were added. The reaction product was filtered and dried in an oven at 70° C. over night. Thus, 1.8 g were obtained. Thereby, an E/Z-ratio of about 12:1 was achieved.

The invention claimed is:

1. A process for the isomerisation of the Z-isomer I-Z of a compound of the general formula I into its E-isomer I-E

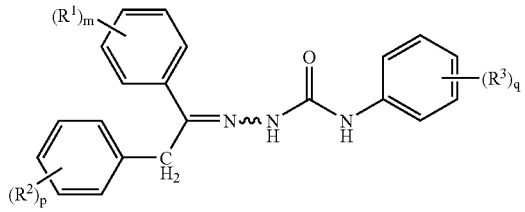

(I)

wherein m, p and q are each independently an integer of 0, 1, 2, 3 or 4

$R^1$, $R^2$, $R^3$ are each independently halogen; OH; CN; $NO_2$;

$C_1$-$C_6$-alkyl, optionally substituted with $C_1$-$C_4$-alkoxy, $C_1$-$C_4$-haloalkoxy or $C_3$-$C_6$-cycloalkyl;

$C_1$-$C_6$-haloalkyl;

$C_3$-$C_6$-cycloalkyl;

$C_1$-$C_6$-alkoxy optionally substituted with $C_1$-$C_4$-alkoxy or $C_3$-$C_6$-cycloalkyl;

$C_1$-$C_6$-haloalkoxy;

$C_1$-$C_6$-alkylcarbonyl;

$C_3$-$C_6$-cycloalkoxy;

$C_1$-$C_6$-alkoxycarbonyl or $C_1$-$C_6$-alkoxycarbonyloxy;

which is characterized in that the Z isomer I-Z or a mixture of the stereoisomers I-Z and I-E is isomerizing with iodine.

2. The process as claimed in claim 1, wherein iodine is used in amounts from 0.1 to 10% by weight, based on the total amount of the compound of the general formula I.

3. The process as claimed in claim 1, wherein the isomerisation is performed in an inert solvent or diluent.

4. The process as claimed in claim 1, wherein the isomerisation is performed in the absence of a solvent or diluent.

5. The process as claimed in claim 1, wherein a mixture of the isomers I-Z and I-E having an E/Z ratio ranging from 15:1 to 2:1 is reacted.

6. The process as claimed in claim 1, wherein the isomerisation is performed at a temperature ranging from 40 to 150° C.

7. The process as claimed in claim 1, where in formula I, m, p, and q are each 1 and $R^1$, $R^2$, $R^3$ are each independently halogen, CN, $C_1$-$C_6$-alkyl, $C_1$-$C_6$-haloalkyl, $C_1$-$C_6$-alkoxy or $C_1$-$C_6$-haloalkoxy.

8. The process as claimed in claim 7, where in formula I, $R^1$ is $CF_3$ located in the 3-position of the phenyl ring, $R^2$ is CN located in the 4-position of the phenyl ring and $R^3$ is $OCF_3$ located in the 4-position of the phenyl ring.

* * * * *